United States Patent
Deimling et al.

(10) Patent No.: US 8,064,671 B2
(45) Date of Patent: Nov. 22, 2011

(54) IMAGING APPARATUS

(75) Inventors: Michael Deimling, Möhrendorf (DE); Sultan Haider, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1004 days.

(21) Appl. No.: 11/418,121

(22) Filed: May 5, 2006

(65) Prior Publication Data

US 2006/0264763 A1  Nov. 23, 2006

(30) Foreign Application Priority Data

May 6, 2005 (DE) .......... 10 2005 021 067

(51) Int. Cl.
*G06K 9/00* (2006.01)
(52) U.S. Cl. .......... 382/131; 324/300; 600/410
(58) Field of Classification Search .......... 382/131; 324/300; 600/410
See application file for complete search history.

(56) References Cited

U.S. PATENT DOCUMENTS

| 4,991,587 A | 2/1991 | Blakeley et al. |
| 5,739,691 A | 4/1998 | Hoenninger, III |
| 2002/0075997 A1 | 6/2002 | Unger et al. |
| 2003/0228042 A1 * | 12/2003 | Sinha .......... 382/131 |
| 2007/0140542 A1 * | 6/2007 | Spahn .......... 382/132 |

FOREIGN PATENT DOCUMENTS

WO   WO 2004/110276   12/2004

OTHER PUBLICATIONS

German Search Report dated Feb. 24, 2006.

* cited by examiner

*Primary Examiner* — Bhavesh Mehta
*Assistant Examiner* — Katrina Fujita
(74) *Attorney, Agent, or Firm* — Harness, Dickey & Pierce, P.L.C.

(57) ABSTRACT

An imaging apparatus is disclosed that displays an image acquired from an examination object. The apparatus includes an acquisition unit that determines image acquisition parameters and acquires the signal values of the examination object; a conversion unit that uses a transfer function to convert the acquired signal values into brightness values that are displayed in the image; a unit for extracting the image acquisition parameters; and a storage unit that has data records in which at least one transfer function is stored in relation to the image acquisition parameters. The conversion unit compares the image acquisition parameters with the image acquisition parameters stored in the storage unit and selects the transfer function as a function of the comparison.

14 Claims, 2 Drawing Sheets

| Measuring sequence | Anatomical region | Finding | Acquisition parameters | Transfer function |
|---|---|---|---|---|
| T2 TIR11 | neck | Glomus tumor | TR, TE, Ti, TA, FOV, MATRIX | nonlinear |
| T1 turbo spin echo | head | glioblastom | TR, TE, TA, FOV, MATRIX | nonlinear quadratic median |

| Measuring sequence | Anatomical region | Finding | Acquisition parameters | Transfer function |
|---|---|---|---|---|
| T2 TIR11 | neck | Glomus tumor | TR, TE, Ti, TA, FOV, MATRIX | nonlinear |
| T1 turbo spin echo | head | glioblastom | TR, TE, TA, FOV, MATRIX | nonlinear quadratic median |

IMAGING APPARATUS

The present application hereby claims priority under 35 U.S.C. §119 on German patent application number DE 10 2005 021 067.8 filed May 6, 2005, the entire contents of which is hereby incorporated herein by reference.

FIELD

The present invention generally relates to an imaging apparatus and/or a method for displaying an image of an examination object. The invention may relate, in particular, to a magnetic resonance installation in which the acquired MR images are displayed as a function of the image acquisition parameters.

BACKGROUND

The known art discloses magnetic resonance installations or MR tomographs in which various contrasts of the examined tissue can be achieved by selecting the image acquisition parameters. For the purpose of display in the MR image, the magnetic resonance signals are detected by coils and displayed on the display screen in a fashion converted into gray scale values.

The purpose of converting the signal values into gray scale values or brightness values is served by a transfer function, also called a filter, that defines conversion of the MR signals into image brightness values. It is mostly linear transfer functions or filters that have been used to date in order to convert the signal values into brightness values. However, a linear transfer function is not the best choice for each diagnostic problem, since other transfer functions possibly enable a better contrast in the acquired image, it being possible thereby, for example, to improve tumor detection and the delimitation of the tumor from the healthy tissue.

SUMMARY

An object of at least one embodiment of the present invention includes improving the display of an image acquired from the examination object such that the diagnostician can more easily interpret the acquired images.

An object may be achieved via an imaging apparatus and/or a method for displaying an image. Example embodiments of the invention are described in the detailed description.

According to at least one embodiment of the invention, the imaging apparatus, which displays an image acquired from an examination object, has an acquisition unit that determines image acquisition parameters and acquires signal values of the examination object. Also provided is a conversion unit that uses a transfer function to convert the acquired signal values into brightness values that are displayed in the image.

Also provided is a unit for extracting the image acquisition parameters. This detects the image acquisition parameters with the aid of which the image was produced.

Also provided is a storage unit that has data records in which at least one transfer function is stored in relation to the image acquisition parameters, the conversion unit comparing the image acquisition parameters that were acquired by the acquisition unit with the image acquisition parameters stored in the storage unit, the transfer function being selected as a function of the comparison. The transfer function determines the contrast in the acquired image. The optimum transfer function can be selected by comparing the image acquisition parameters with the data records in the storage unit, since image acquisition parameters that have been successful in displaying specific problems are stored with associated transfer function in the storage unit.

The imaging apparatus may include a magnetic resonance installation, the unit for extracting the image acquisition parameters extracting at least one of the following image acquisition parameters: echo time, repetition time, field of view, inversion time, acquisition time, slice thickness, matrix size, name of the imaging sequence. All these image acquisition parameters named by way of example exert a greater or lesser influence on the contrast in the displayed MR image. By determining at least a few of these parameters, it is subsequently possible to select a transfer function or a filter function that fits the image acquisition parameters and amplifies the desired contrast in the examined tissue.

In a further example embodiment, the selection of the transfer function can be influenced by the anatomical region that is displayed in the image. To this end, it is possible to provide an image processing unit that infers the displayed anatomy from the acquired image of the examination object. This can be performed by way of known pattern recognition algorithms that can, for example, use edge detection or similar methods to infer the anatomical region displayed in the MR image.

In a further example embodiment, the selection of the transfer function can also be made dependent on the identity of the operator. Thus, different operators or diagnosticians prefer different transfer functions or filters in order to clarify specific clinical problems. The identity of the operator must be known to this end, and so it is possible to provide a unit for determining the operator that identifies the operator. This can be performed, for example, by having the operator of the imaging apparatus identified by a code. When selecting the transfer function, consideration is given as a function of the operator to the data records in the case of which acquisition parameters are stored with associated transfer functions that are used by this operator for specific problems.

An example embodiment of the invention relates to a method for displaying an image that is acquired by the imaging apparatus from the examination object. Here, the imaging apparatus acquires an image by detecting signal values. Subsequently, for this image the signal values are converted into brightness values that are displayed in the image, a transfer function being used for the conversion. Likewise, the image acquisition parameters used in signal acquisition are determined, and the transfer function is subsequently selected for displaying the signal values with the aid of brightness values as a function of the acquisition parameters of the image. Consequently, the image is displayed with the aid of the selected transfer function. By selecting the transfer function as a function of the image acquisition parameters, it is possible to select the suitable filtering that is best for the respective clinical problem.

The acquisition parameters of the image are preferably compared with acquisition parameters in a memory in which the image acquisition parameters are stored with an associated transfer function, the transfer function for displaying the brightness values being selected as a function of the comparison.

In an example embodiment, the transfer function is determined for an MR image. In order to select this transfer function, it is possible, furthermore, to determine the weighting in the MR image, the transfer function being inferred from the weighting (for example, T1 weighted, T2 weighted, proton-density weighted). It has emerged for specific weightings that specific transfer functions result in a better contrast than other transfer functions.

Furthermore, it is possible to determine the anatomy of the examination object that is displayed in the image. The selection of the transfer function is then performed as a function of the acquired anatomical region.

Furthermore, in accordance with a further embodiment, not only is a transfer function selected for displaying the acquired image, but it is possible to select a number of transfer functions and to display the images with the aid of this number of transfer functions. For example, in addition to known linear transfer functions it is also possible to use nonlinear functions, quadratic functions and/or median filters, the images being displayed with the aid of the different filters, in order to facilitate interpretation of the images for the diagnostician.

In accordance with a further inventive embodiment, once the diagnostician has selected the relationship between image acquisition parameters and transfer functions it can be stored such that this data record can be used for future applications. Should a similar anatomical region be acquired with the aid of similar image acquisition parameters, the transfer function used at an earlier instance can then be used to display the image.

BRIEF DESCRIPTION OF THE DRAWINGS

Example embodiments of the invention are described in more detail below with reference to the attached drawings, in which.

DETAILED DESCRIPTION OF THE EXAMPLE EMBODIMENTS

Figure 1:
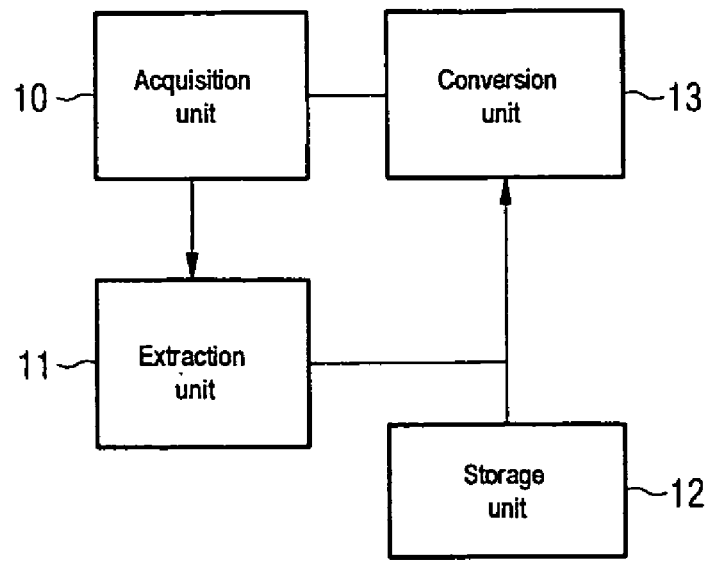
FIG. 1 shows a schematic apparatus for displaying an image in accordance with at least one embodiment of the invention.

FIG. 1 is a schematic of the imaging apparatus. The apparatus has an acquisition unit 10 that determines the image acquisition parameters and acquires the signal values of the examination object. In the case of a magnetic resonance installation, the design of the image acquisition unit is known to the person skilled in the art, and so it is possible to dispense with a more accurate description. The voltage signal detected by the coil is to be converted into an MR image.

Provided for this purpose is an extraction unit 11 that detects the image acquisition parameters such as echo time, repetition time, inversion time, acquisition time, slice thickness, matrix size, etc. and the names of the imaging sequence. This is possible, for example, since these image acquisition parameters are contained in the header of an MR data record. The parameters used in the image acquisition are then compared with the data records that are stored in a storage unit 12.

These data records are described later in conjunction with FIG. 3. For example, image acquisition parameters are stored with the associated transfer function in the storage unit 12. This transfer function is extracted by the extraction unit 11 and transmitted to a conversion unit 13 that converts the acquired signal values into brightness values and displays these brightness values in the image, the transfer function being selected by comparing the image acquisition parameters of the acquisition unit 10 with the image acquisition parameters stored in the storage unit 12, and with the aid of associated transfer functions.

Figure 2:
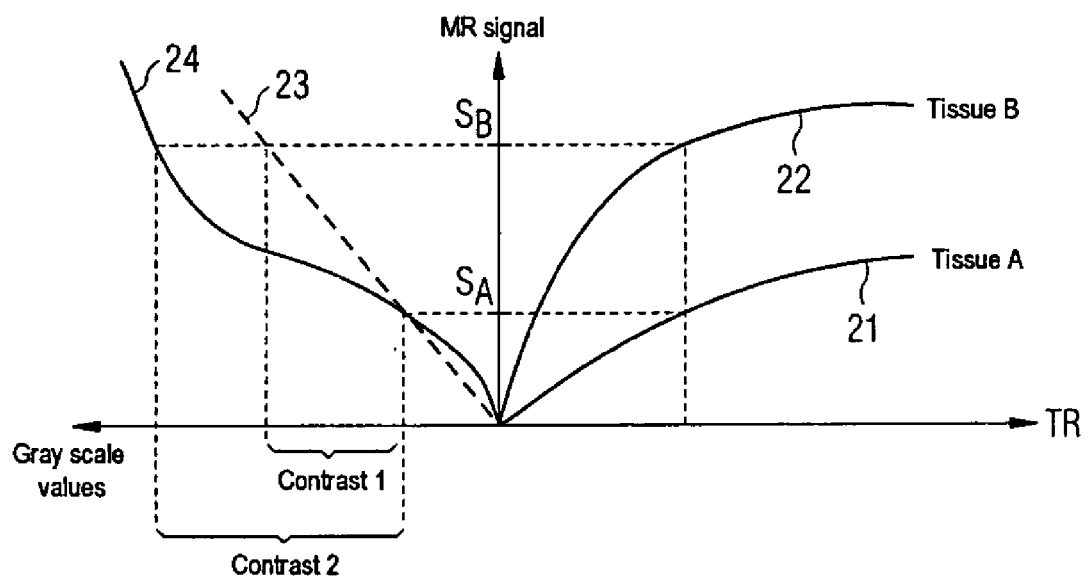
FIG. 2 shows the relationship between MR signal and the displayed gray scale values.

How the selection of the transfer function influences the contrast in image is illustrated in FIG. 2. The signal profile of the tissue A plotted against the repetition time TR is illustrated on the right-hand side of the graph by the curve 21. The signal profile for the tissue B is illustrated in the curve 22. Emerging therefrom in relation to a specific repetition time TR is an MR signal $S_A$ and an MR signal $S_B$ that is then displayed in the MR image in brightness values or gray scale values.

A transfer function that influences the transfer of the signal values into gray scale values is used for the purpose of converting the MR signal into gray scale values. The linear transfer function 23 is illustrated by dashes on the left-hand side of FIG. 2. For the MR signals $S_A$ and $S_B$ the selection of linear transfer function 21 produces a first contrast that is denoted as contrast 1 in FIG. 2. However, if a nonlinear transfer function 24 is selected, a greater contrast 2 results for the MR signals $S_A$ and $S_B$.

As illustrated by way of example in FIG. 2, the contrast behavior in the image can be improved by selecting the suitable transfer function. This transfer function, also termed filter, can assume various functions. This function can be approximated in a series expansion, for example. The transfer function F(x) can then be approximated, for example, in such a way that:

$$F(x)=a_0+a_1x+a_2x^2+a_3x^3+a_4x^4+a_nx^n+\ldots$$

Of course, other known filter functions are also possible.

Figures 3, 4:
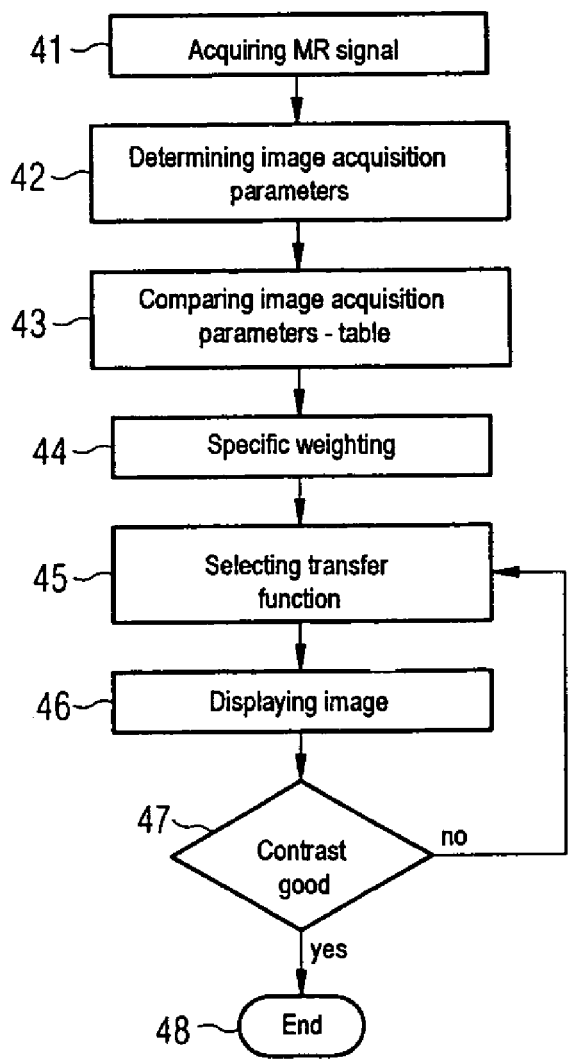
FIG. 3 shows an example embodiment of data records for determining the transfer function.
FIG. 4 shows a flowchart for determining the brightness values in an acquired image.

FIG. 3 illustrates by way of example a section of a table such as could be stored in the storage unit 12. The table includes two data records in the embodiment illustrated. The first data record specifies which transfer function could be selected when examining the neck in order to detect a glomus tumor by using a T2 TIRM sequence.

In the present case, it is possible to infer that a nonlinear transfer function is advantageous for the display by detecting some acquisition parameters of the measuring sequence used in the magnetic resonance installation, for example by determining the repetition time TR, the echo time TE, the inversion time TI, the acquisition time TA, the matrix used or the field of view FOV used. The anatomic region displayed in the image can be determined, for example, by use of a image processing unit that can infer the anatomy displayed by means of known image processing methods.

The transfer function that is included in the table of FIG. 3 can be selected when, on the one hand, an item of information included in columns 1 to 4 relates to the acquired MR image. It is likewise possible to select the transfer function only when the information included in columns 1 to 4 relates. In addition to the nonlinear transfer function proposed in this example embodiment, it is possible, for example, to use a conventional linear transfer function for display purposes such that two MR images of different contrast are displayed, and this can facilitate the diagnosis of the images.

As is to be seen from the second data record of FIG. 3, it is also possible to propose a number of transfer functions. In the example embodiment illustrated, a nonlinear transfer function, a quadratic transfer function and a median transfer function are proposed for a turbo spin echo imaging sequence with TZ weighting in the case of imaging the head giving specific acquisition parameters. For example, MR images can be produced for all these transfer functions so that a diagnosis can be made from the different contrast behavior.

FIG. 4 illustrates the different steps that are required for selecting the correct transfer function. In a first step 41, the MR signal is acquired. Subsequently, the image acquisition parameters used in imaging are determined in a step 42. In a consequent step 43, the image acquisition parameters of the MR image are then compared with the data records stored in the storage unit 12 in order to be able to infer the transfer function from the image acquisition parameters.

In a subsequent step 44, it is possible by way of example to infer the weighting of the MR image from the image acquisition parameters, the weighting (T1 weighted, T2 weighted, proton-density weighted) then providing a reference point as to which transfer function is to be selected for displaying the signal values. In addition to the weighting specified in step 44, it is also possible to detect the anatomical position of the examination region that is to be displayed in the MR image.

Of course, this information can also additionally be used for weighting in order to select the transfer function. The transfer function is subsequently selected in step 45, in order to display the signal values in the image in gray scale or color values in step 46. If the contrast displayed to the diagnostician in the image is sufficient (problem in step 47), the method is ended in step 48. If this is not the case, a further transfer function can be selected in step 45, the image then being displayed with the aid of another transfer function stored in the data record.

It is possible furthermore, for the diagnostician to select a transfer function himself, in order to display the MR image. This transfer function can then be stored in the storage unit 12 together with the associated image acquisition parameters. In this way, the diagnostician gradually produces data records that are helpful in evaluating the images, since they facilitate the display of an anatomical region with a different contrast.

The operator can further be stored in the table illustrated in FIG. 3, and so the transfer functions desired by the operator can be selected as a function of the latter.

The system can thus learn from the selection of the transfer function. The data records stored in the storage unit facilitate the production of an outlet in which the filter functions are listed for various sequence parameters and for various anatomical regions.

In summary, embodiments of the present invention may facilitate the display of an image with a different contrast, it being possible to display the images with the contrast behavior that is desired by a diagnostician by comparing the image acquisition parameters with data records that exhibit image acquisition parameters with associated transfer function. Of course, embodiments of the present invention are not limited to magnetic resonance installations. It is also possible to apply embodiments of the invention with other imaging systems in the case of which image acquisition parameters influence the acquired signal.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. An imaging apparatus to display an image acquired from an examination object, the apparatus comprising:
    an acquisition unit to determine image acquisition parameters and to acquire image signal values of the examination object;
    a conversion unit to, using a transfer function, convert the acquired image signal values into brightness values displayed in the image;
    a unit to extract the image acquisition parameters; and
    a storage unit to store at least one transfer function in relation to image acquisition parameters, the conversion unit being configured to compare the extracted image acquisition parameters with the image acquisition parameters stored in the storage unit and select the transfer function as a function of the comparison; wherein
        the imaging apparatus is a magnetic resonance installation,
        the unit to extract the image acquisition parameters is configured to extract at least one of the following image acquisition parameters: echo time, repetition time, field of view, inversion time, acquisition time, slice thickness, matrix size, and name of an imaging sequence, and
        the acquired image signal values are Fourier transformed image signal values.

2. The apparatus as claimed in claim 1, further comprising:
    an image processing unit to infer, from the acquired image of the examination object, the anatomy in the examination object displayed in the image, the anatomical information being considered when selecting the transfer function.

3. The apparatus as claimed in claim 1, wherein a unit for determining an operator is provided, the identity of the operator being considered when selecting the transfer function.

4. The apparatus as claimed in claim 3, further comprising:
    an image processing unit to infer, from the acquired image of the examination object, the anatomy in the examination object displayed in the image, the anatomical information being considered when selecting the transfer function.

5. The apparatus as claimed in claim 4, wherein the transfer function is selected as a function of the anatomical region.

6. The apparatus as claimed in claim 4, wherein at least two different transfer functions are selected as a function of the comparison, the images being displayed with the aid of the at least two different transfer functions.

7. The apparatus as claimed in claim 4, wherein the image parameters of an image are stored in the memory with the aid of the transfer function selected by a diagnostician such that the stored data record is considered when next selecting the transfer function as a function of the comparison.

8. A method for displaying an image acquired from an examination object, the method comprising:
- acquiring an image by detecting image signal values;
- converting, via a transfer function, the detected image signal values into brightness values displayed in the image;
- determining acquisition parameters used in signal acquisition; and
- selecting the transfer function, for displaying the image signal values in brightness values, as a function of the determined acquisition parameters of the image, wherein the selected transfer function is used to display the image; wherein
  - the acquisition parameters of the image are compared with acquisition parameters in a memory, in which the acquisition parameters are stored with an associated transfer function, the transfer function for displaying the brightness values being selected as a function of the comparison,
  - the image is produced with the aid of nuclear magnetic resonance,
  - the acquisition parameters are determined during image acquisition, and include at least one of echo time, repetition time, field of view, inversion time, acquisition time, slice thickness, matrix size, and name of the imaging sequence, and
  - the detected image signal values are Fourier transformed image signal values.

9. The method as claimed in claim 8, wherein weighting of the acquired MR image is determined from the acquisition parameters.

10. The method as claimed in claim 8, further comprising:
- determining an anatomical region, displayed in the image, of the examination object, the transfer function being selected as a function of the anatomical region.

11. The method as claimed in claim 8, wherein at least two different transfer functions are selected as a function of the image acquisition parameters, the images being displayed with the aid of the at least two different transfer functions.

12. The method as claimed in claim 8, wherein the image parameters of an image are stored in the memory with the aid of the transfer function selected by a diagnostician such that the stored data record is considered when next selecting the transfer function as a function of the acquisition parameters.

13. An imaging apparatus to display an image acquired from an examination object, the apparatus comprising:
- means for determining image acquisition parameters and for acquiring image signal values of the examination object;
- means for, using a transfer function, converting the acquired image signal values into brightness values displayed in the image;
- means for extracting the image acquisition parameters; and
- means for storing at least one transfer function in relation to image acquisition parameters, the means for converting being for comparing the extracted image acquisition parameters with the stored image acquisition parameters and for selecting the transfer function as a function of the comparison; wherein
  - the imaging apparatus is a magnetic resonance installation,
  - the means for extracting the image acquisition parameters is for extracting at least one of the following image acquisition parameters: echo time, repetition time, field of view, inversion time, acquisition time, slice thickness, matrix size, and name of an imaging sequence, and
  - the acquired image signal values are Fourier transformed image signal values.

14. The apparatus as claimed in claim 13, further comprising:
- means for inferring, from the acquired image of the examination object, the anatomy in the examination object displayed in the image, the anatomical information being considered when selecting the transfer function.

* * * * *